United States Patent [19]

Cebalo et al.

[11] Patent Number: 4,876,044
[45] Date of Patent: Oct. 24, 1989

[54] THIADIAZOLE COMPOUNDS AND METHODS OF USE

[76] Inventors: Tony Cebalo, 7244 Sondridge Cir., Indianapolis, Ind. 46205; Robert E. Buntrock, 546 N. Webster St., Naperville, Ill. 60540

[21] Appl. No.: 863,338

[22] Filed: Oct. 2, 1969

[51] Int. Cl.⁴ .................. A01N 43/82; C07D 285/12
[52] U.S. Cl. ........................................ 71/90; 548/140
[58] Field of Search .................................. 260/306.80

[56] References Cited
PUBLICATIONS

Claim 1 of South African Patent 68/5647; So. African Patent Journal; Mar., 1969.

Primary Examiner—Glennon H. Hollrah
Assistant Examiner—S. Treanor
Attorney, Agent, or Firm—Leroy Whitaker

[57] ABSTRACT

Novel thiadiazole compounds are produced having the following general formula:

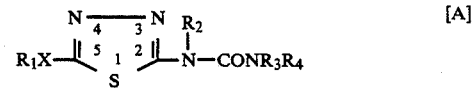

wherein
- X is S or $SO_2$
- $R_1$ is a lower alkyl (cyclic or non-cyclic) radical
- $R_2$ is hydrogen or a lower acyclic hydrocarbon radical
- $R_3$ is a lower acyclic hydrocarbon or cycloalkyl radical or alkoxy radical, and
- $R_4$ is hydrogen, a lower acyclic hydrocarbon radical or cycloalkyl radical, provided $R_3$ and $R_4$ are not both cycloalkyl, and

[B] Tautomers of [A] wherein $R_2$ is hydrogen.

Synthesis of these compounds is disclosed, including synthesis of those compounds which exhibit tautomerism.

The compounds show particular utility as agricultural pesticides and most favorably as herbicides.

16 Claims, No Drawings

THIADIAZOLE COMPOUNDS AND METHODS OF USE

BACKGROUND OF THE INVENTION

This invention relates to thiadiazoles. More particularly, it relates to thiadiazol-2-yl ureas containing, for example, an alkyl sulfide or alkyl sulfonyl group in the 5-position.

The prior art is replete with thiadiazoles and various derivatives thereof. However, none are belived to have the types of activities claimed in the present invention. The few somewhat related compounds shown in the prior art such as, for example, 1-(5-methyl-1,3,4-thiadiazol-2-yl)-3-phenylthiourea and 1-(5-methyl-1,3,4-thiadizaol-2-yl)-3-phenylurea [J. Pharm. Soc. Japan, 74, 1044–8 (1954); CA 11630] were not reported to have biological activity. Compounds similar to the present invention are also disclosed in Belgian Pat. No. 721,034.

An article in Farmaco Ed. Sci. 22 (6), 393–401 (1967) discloses the use of 1-(50alkyl-1,3,4-thiadiazol-2-yl)ureas as intermediates for the production of isomeric 1,3-bis-(5-alkyl-1,3, 4-thiadiazol-2-yl)ureas which latter compounds are alleged to exhibit hypoglycemic action. These compounds are only generally related to those of the instant invention.

SUMMARY OF THE INVENTION

The invention pertains to thiadiazoles and derivatives thereof which have utility as agricultural pesticides. The thiadiazoles may be represented most broadly, as having the structure:

[A]

$$R_1X-\underset{S}{\underset{\|}{\overset{N\underline{\qquad}N}{\|}}}-\underset{\underset{H}{|}}{N}-\overset{O}{\overset{\|}{C}}-NR_3R_4 \quad (I)$$

where
X is S or $SO_2$
$R_1$ is a lower alkyl (cyclic or non-cyclic)radical.
$R_2$ is hydrogen or a lower acyclic hydrocarbon radical
$R_3$ is a lower acyclic hydrocarbon radical, a cycloalkyl radical or an alkoxy radical, and
$R_4$ is hydrogen, a lower acyclic hydrocarbon radical, or cycloalkyl radical, provided $R_3$ and $R_4$ are not both cycloalkyl, and

[B] Tautomers of [A] wherein $R_2$ is hydrogen

It is to be understood that in Structure I above, where $R_2$ is hydrogen, it may exist in the tautomeric form $$R_1X-\underset{S}{\underset{\|}{\overset{N\underline{\qquad}NH}{\|}}}=NCONR_3R_4$$

where $R_1$, $R_3$ and $R_4$ have the designations hereinbefore set forth. Therefore, in compositions of the invention where $R_2$ is hydrogen, the above tautomeric structure is always implied to exist.

The symbols $R_1$, $R_2$, $R_3$ and $R_4$ will have the same meaning throughout the entirety of the specification and claims.

The compounds show excellent activity as agricultural pesticides, particularly as herbicides, for controlling a broad spectrum of unwanted and undesirable weeds and plants.

PREFERRED EMBODIMENTS OF THE INVENTION

Methods of Synthesis

Generally, the compounds of the present invention may be prepared by one or more of the synthesis routes set forth below. The type of product desired will determine the particular synthesis route to be employed.

$$HS-\underset{S}{\underset{\|}{\overset{N\underline{\qquad}N}{\|}}}-NHR_2 \longrightarrow HS-\underset{S}{\underset{\|}{\overset{N\underline{\qquad}N}{\|}}}-\underset{\underset{}{|}}{\overset{R_2}{N}}CONR_3R_4$$
(II) (IV)

$$\downarrow \qquad\qquad \downarrow$$

$$R_1S-\underset{S}{\underset{\|}{\overset{N\underline{\qquad}N}{\|}}}-NHR_2 \longrightarrow R_1S-\underset{S}{\underset{\|}{\overset{N\underline{\qquad}N}{\|}}}-\underset{\underset{}{|}}{\overset{R_2}{N}}CONR_3R_4$$
(III) (V)

$$\downarrow \qquad\qquad \downarrow$$

$$R_1SO_2-\underset{S}{\underset{\|}{\overset{N\underline{\qquad}N}{\|}}}-NHR_2 \longrightarrow R_1SO_2-\underset{S}{\underset{\|}{\overset{N\underline{\qquad}N}{\|}}}-\underset{\underset{}{|}}{\overset{R_2}{N}}CONR_3R_4$$
(VII) (VI)

The intermediate compositions corresponding to Structure (II) are synthesized by methods known in the art. For example, such methods are generally taught in publications such as "The Chemistry of Heterocyclic Compounds" V. 4 L. L. Bambas, Interscience Publishers, Inc., New York, 1952 and Petrow et. al. J. Chem. Soc. 1508 (1958). The intermediate compounds having the Structure (III) and (V) may be synthesized from compounds (II) and (IV) by known methods, e.g. reacting compounds (II) and (IV) with alkyl halides and dialkyl sulfates in the presence of a base such as potassium carbonate, sodium hydroxide, potassium hydroxide and the like.

Compounds having the ureido moieties, as shown above, may be synthesized by several methods which are known in the art. For example, compounds (II), (III) and (VII) may be reacted with an isocyanate in an inert solvent such as benzene, N,Ndimethylformamide, ethyl acetate and the like. A catalyst such as triethylamine may be employed in the reaction $$RX-\underset{S}{\underset{\|}{\overset{N\underline{\qquad}N}{\|}}}-NHR_2 + R_3NCO \xrightarrow{(C_2H_5)_3N}$$

$$RX-\underset{S}{\underset{\|}{\overset{N\underline{\qquad}N}{\|}}}-\underset{\underset{}{|}}{\overset{R_2}{N}}CONHR_3$$

wherein R is H or $R_1$ and X is as previously defined.

Another method of synthesis is that in which a carbamoyl chloride is reacted with an amine in the presence of an acid-fixing agent such as sodium carbonate, triethylamine, pyridine and the like, e.g. the amines (III) or (VII), are reacted to obtain the final products of the invention. The same reaction may be conducted in a slightly different manner wherein a metal derivative of an amine is reacted with a carbamoyl chloride to give the desired product. The reaction may be conducted in inert solvents such as benzene, tetrahydrofuran, dimethyl formamide, dioxane and the like.

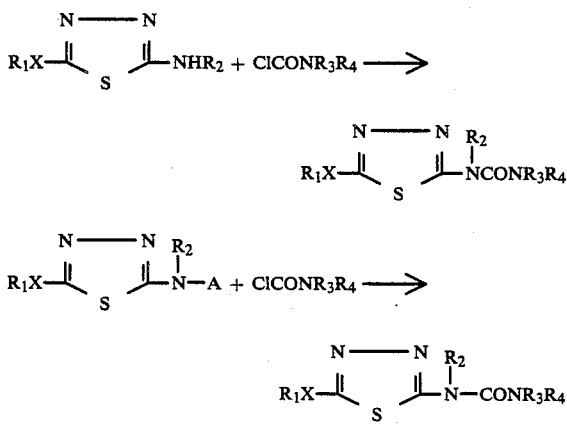

A = Na, K or Li

Another reaction that may be developed to produce the final products of the invention is one in which N,N'-carbonyldimidazole is reacted with an intermediate thiadiazole compound to produce an intermediate isocyanate product which in turn is reacted with an amine to produce the desired final product.

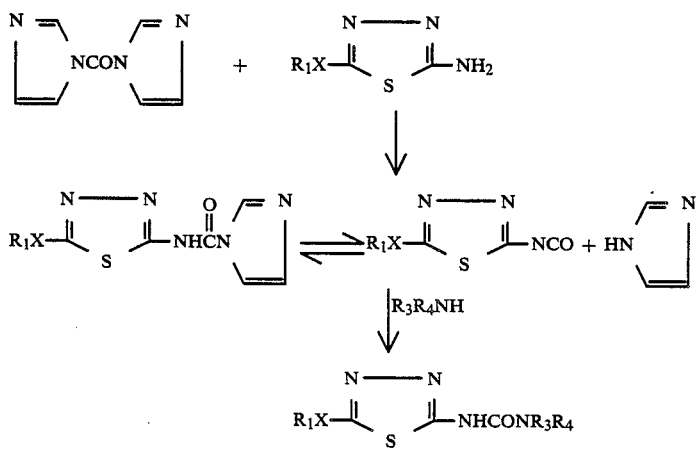

In still another reaction, phosgene (COCl$_2$) may be reacted with a thiadiazole amine to produce a carbamoyl chloride product which in turn is reacted with a primary or secondary amine to produce a product of the invention. The above-described reaction may be conducted in the presence of a base, e.g. tertiary amine, and/or a catalyst such as boron trifluoride-ether complex. The reactions may also be conducted in inert solvents such as aromatic hydrocarbons, N,N-dimethylformamide, tetrahydrofuran and the like.

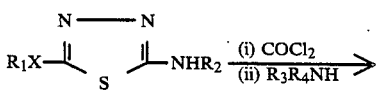

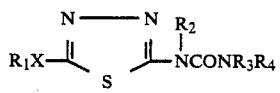

It is understood that the method employed will depend upon the particular intermediate selected for producing the corresponding intermediate or desired final product.

The alkylmercapto compounds of Structure (V) may be oxidized to the corresponding sulfones of Structure (VI) by oxidizing with reagents such as chlorine-acetic acid, chlorine-ferric chloride, potassium permanganate, hydrogen peroxide-acetic acid and the like.

The final products of the invention corresponding to the Structure (I), wherein R$_2$ is hydrogen, form metal and ammonium salts (substituted or unsubstituted) corresponding to the Structure (VIII) below. For polyvalent metals, the salt compounds are chelate in character. The alkali metal and ammonium salts provide highly desirable properties such as water solubility when employed for use in agricultural applications. In addition, the alkali metal salt compositions will react with reactive halogen compounds, e.g. alkyl halides to provide compounds having the general formula of Structures (I) and (IX) where R$_2$ is not hydrogen.

(VIII)

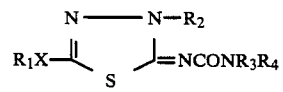

(IX)

Y = metal or ammonium radical
n = equivalence of Y, e.g. where Y = Na, K, Li, n = 1.

In the compounds of the present invention, it is preferred that R$_1$ as a lower alkyl radical contain from 1 to 4 carbon atoms; R$_2$ as a lower alkyl radical contain from 1 to 4 carbon atoms; R$_3$ as a lower alkyl radical contain from 1 to 4 carbon atoms, as a cycloalkyl radical contain 3 to 6 carbon atoms and as an alkoxy radical contain from 1 to 4 carbon atoms and R$_4$ as a lower alkyl radical contain from 1 to 4 carbon atoms.

The following examples are illustrative of the invention and are not intended to limit the scope thereof.

EXAMPLE 1

A mixture containing 30 gm of 2-(N-methylamino)-5-mercapto-1,3,4-thiadiazole and 11.60 gm of methyl isocyanate in 250 ml of benzene was refluxed in a 500 ml flask for a period of about 2 hours. The resulting mixture was cooled and filtered to obtain 40 gm of a product having a melting point of 162°–164° C. and identified to be 1,3-dimethyl-3-(5-mercapto-1,3,4-thiadiazol-2-yl)urea.

EXAMPLE 2

A mixture containing 5 gm of 1,3,-dimethyl-3-(5-mercapto-1,3,4-thiadiazol-2-yl)urea, 3.7 gm of methyl iodide and 1.7 gm of anhydrous potassium carbonate in 50 ml of N,N-dimethylformamide stirred for about 15 hours at a temperature of about 70° C. The resulting clear mixture was concentrated under vacuum to a solid which on recrystallization from ethyl acetate yielded a product identified to be 1,3-dimethyl-3-(5-methylmercapto-1,3,4-thiadiazol-2-yl)urea having a metling point of 154°–156° C.

EXAMPLE 3

To a suspension containing 5 gm of 1,3-dimethyl-3-(5-methylmercapto-1,3,4-thiadiazol-2-yl)urea and 50 ml of acetic acid was added dropwise and with stirring, an aqueous solution of potassium permanganate (7.3 gm in 100 ml of water), said mixture being cooled in an ice-/water bath. The resulting mixture was stirred for about 15 hours at room temperature after which time sodium bisulfite was added until the mixture became colorless. The solid product was recovered by filtering and subsequently recrystallized from methanol to obtain a product identified to be 1,3-dimethyl-3-(5-methylsulfonyl-1,3,4-thiadiazol-2-yl)urea and having a melting point of 182°–183° C.

EXAMPLE 4

A mixture containing 45.1 gm of 2-(N-methylamino)-5-butylmercapto-1,3,4-thiadiazole and 13.9 gm of methyl isocyanate was refluxed in benzene, with stirring, for about 3 hours. The resulting mixture was concentrated under vacuum and the residue recrystallied from aqueous methanol. The final product was identified as 1,3-dimethyl-3-(5-butylmercapto-1,3,4-thiadiazol-2-yl)urea having a melting point of 63°–65° C.

EXAMPLE 5

Into a three-necked round bottom flask equipped with a mechanicl stirring means and bubbling tube were placed 35.9 gm of 1,3-dimethyl-3-(5-butylmercapto-1,3,4-thiadiazol-2-yl)urea and 5 gm of ferric chloride hexahydrate in 500 ml of water. The mixture was cooled to 5° C and a steady stream of chlorine was bubbled through the mixture for about 20 minutes while maintaining the temperature at from 7°–9° C. Nitrogen was subsequently bubbled through the mixture to remove excess chlorine. The mixture was filtered and the solid product recrystallied from aqueous methanol to provide a product identified as 1,3,-dimethyl-3-(5-butylsulfonyl-1,3,4-thiadiazol-2-yl)urea and having a melting point of 123°–124° C.

EXAMPLE 6

To a stirred solution containing 10 gm of N,N'-carbonyldiimidazole in 200 ml of dry tetrahydrofuran was added 9.1 gm of 2-amino-5-methylmercapto-1,3,4-thiadiazole, the mixture being stirred for an additional 30 minutes under a nitrogen atmosphere and subsequently refluxed. The mixture was cooled to room temperature and 18.7 gm of triethylamine followed by 18.0 gm of dimethyl hydroxylamine hydrochloride were added. After stirring for 15 minutes, the mixture was poured into an ice/water mixture and extracted with ethyl acetate. The extracted portion was dried over anhydrous sodium sulfate and subsequently concentrated under vacuum to a residual oil which solidified on standing. The final product was recrystallied from methanol and was identified to be 1-methyl-1-methoxy-3-(5-methylmercapto-1,3,4-thiadiazol-2-yl)urea having a melting point of 97°–100° C.

EXAMPLE 7

To a stirred solution containing 10.1 gm of 1-methyl-3-(5-methylmercapto-1,3,4-thiadiazol-2-yl)urea and 50 gm of glacial acetic acid, heated to 85°–90° C, was added, over a period of about 15 minutes, 14.5 gm of 30% hydrogen peroxide. The temperature was maintained for an additional period of one hour and the mixture was cooled to room temperature. The cooled reaction mixtue was poured into an ice/water mixture and extracted with ethyl acetate. The extracted mixture was dried over anhydrous sodium sulfate and concentrated under vacuum to yield a product identified to be 1-methyl-1-methoxy-3-(5-methylsulfonyl-1,3,4-thiadiazol-2-yl)urea and having a melting point of 146°–148° C.

EXAMPLE 8

To a well stirred mixture containing 20 gm of 2-amino-5-methylmercapto-1,3,4-thiadiazole and 18.4 gm of N-methyl-N-butylcarbamoyl chloride and which had been cooled to about 5° C. was slowly added 4.7 gm of sodium hydride. The reaction mixture was slowly poured into an ice/water mixture and the total mixture extracted with chloroform. The extracted portion was concentrated under vacuum to yield a product which on recrystallization from ethanol provide a product identified as 1-methyl-1-butyl-3-(5-methylmercapto-1,3,4-thiadiazol-2-yl)urea and having a melting point of 93°–94° C.

EXAMPLE 9

A stirred mixture containing 9.3 gm of 1-butyl-1-methyl-3-(5-methylmercapto-1,3,4-thiadiazol-2-yl)urea and 5.0 gm of ferric chloride in 400 ml of water was cooled to about 5° C. and chlorine gas was bubbled through the mixture for about 30 minutes. Nitrogen was bubbled through the mixture to remove excess chlorine and the percipitate separated from the solution by filtration. The percipitation was recrystallized from solox to produce the final product identified as 1-butyl-1-methyl-3-(5-methylsulfonyl-1,3,4-thiadiazol-2-yl)urea and having a melting point of 125°–126° C.

Other examples for the preparation of representative compounds of the invention, as produced in accordance with the methods hereinbefore described, are presented in Table I and II below.

TABLE I

Compounds corresponding to the general formula:

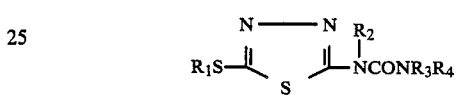

| Example No. | $R_1$ | $R_2$ | $R_3$ | $R_4$ | Melting Point, °C. |
|---|---|---|---|---|---|
| 10 | $CH_3$ | H | $CH_3$ | H | 209–210 |
| 11 | $CH_3$ | $CH_3$ | $CH_3$ | $CH_3$ | oil |
| 12 | $CH_3$ | $CH_3$ | $n\text{-}C_4H_9$ | H | 104–105 |
| 13 | $CH_3$ | $CH_3$ | $CH_3$ | $n\text{-}C_4H_9$ | oil |
| 14 | $CH_2=CHCH_2$ | $CH_3$ | $CH_3$ | H | 125–128 |
| 15 | $(CH_2)_5CH$ | $CH_3$ | $CH_3$ | H | 112–114 |
| 16 | $(CH_3)_2CH$ | $CH_3$ | $CH_3$ | H | 119–120 |
| 17 | $CH_3CH_2CHCH_3$ | $CH_3$ | $CH_3$ | H | 118–119' |
| 18 | $CH_3CH_2CH_2$ | $CH_3$ | $CH_3$ | H | 107–108 |
| 19 | $CH_3CH_2$ | $CH_3$ | $CH_3$ | H | 112–113 |

TABLE II

Compounds corresponding to the formula

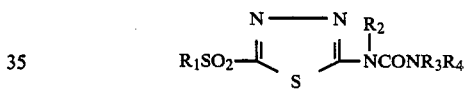

| Example No. | $R_1$ | $R_2$ | $R_3$ | $R_4$ | Melting Point, °C. |
|---|---|---|---|---|---|
| 20 | $CH_3$ | H | $CH_3$ | H | 214–215 |
| 21 | $CH_3$ | H | $CH_2CH=CH_2$ | H | 171–174 |
| 22 | $CH_3$ | H |  | H | 167–169 |
| 23 | $CH_3$ | $CH_3$ | $CH_3$ | $n\text{-}C_4H_9$ | oil |
| 24 | $(CH_2)_5CH$ | $CH_3$ | $CH_3$ | H | 183–184 |
| 25 | $CH_3CH_2CHCH_3$ | $CH_3$ | $CH_3$ | H | 178–179 |
| 26 | $CH_3CH_2CH_2$ | $CH_3$ | $CH_3$ | H | 138–139 |

Biological Activity of Final Products

The herbicidal activity of products of the invention were tested in accordance with the procedure hereinafter set forth. For pre-emergence testing the soil in which seeds were planted were spryaed the same day with a solution containing the designated amount of product in a 50–100% acetone-water mixture. Observations of activity were recorded twenty-one (21) to twenty-eight (28) days after planting and spraying. For post-emergence testing the plants were sprayed with the same solution as described above about fourteen (14) days after planting of the seeds. A vigor and kill rating was adopted to assess the phytotoxic properties of the products. For both testing procedures a percent kill rating for each species of plants was compared with untreated control plants growing under similar conditions. A vigor rating of 1 to 5 was also given to surviving plants not killed by chemical treatment and is defined as follows:

1. severe injury, plants will die
2. moderate injury, plants will not recover
3. moderate injury, plants will recover
4. slight injury, plants will or have recovered and will resume normal growth
5. no apparent injury The following tables show the pre- and post-emergent herbicidal activity of compounds of the invention.

Tables I and II show pre- and post-emergence activity respectively of compounds of the general formula:

$$R_1S\underset{S}{\overset{N----N}{\bigwedge}}NCONR_3R_4 \;\; | R_2$$

and Tables III and IV show pre- and post-emergent activity respectively of compounds of the general formula:

$$R_1SO_2\underset{S}{\overset{N----N}{\bigwedge}}NCONR_3R_4 \;\; | R_2$$

The evaluated plant species are identified below as to their corresponding Latin names:
Sugar Beets: *Beta vulgaris*
Corn: *Zea mays*
Oats: *Avena sativa*
Clover: *Melilotus indica*
Soybeans: *Glycine max*
Cotton: *Gossypium hirsutum*
Mustard: *Brassica juncea*
Yellow Foxtail: *Setaria glauca*
Barnyardgrass: *Echinochloa crusgalli*
Crabgrass: *Digitaria sanguinalis*
Buckwheat: *Fagopyrum tataricum*
Morningglory: *Ipomoca purpurca*

TABLE I

PRE-EMERGENT ACTIVITY

| PRODUCT OF EXAMPLE NO. | LBS. PER ACRE | Sugar Beets | | Corn | | Oats | | Clover | | Soybeans | | Cotton | | Mustard | | Yellow Foxtail | | Barnyard Grass | | Crab Grass | | Buck-Wheat | | Morning-Glory | |
|---|---|---|---|---|---|---|---|---|---|---|---|---|---|---|---|---|---|---|---|---|---|---|---|---|---|
| | | Vig | %Kill | Vig | %Kill | Vig | %Kill | Vig | %Kill | Vig | %Kill | Vig | %Kill | Vig | %Kill | Vig | %Kill | Vig | %Kill | Vig | %Kill | Vig | %Kill | Vig | %Kill |
| 4 | 4 | — | 100 | 4 | 0 | — | 100 | — | 100 | — | 100 | — | 100 | — | 100 | — | 100 | 2 | 40 | — | 100 | — | 100 | — | 100 |
| | 2 | — | 100 | 4 | 0 | — | 90 | — | 100 | — | 50 | — | 100 | — | 100 | — | 20 | 2 | 20 | — | 90 | — | 100 | — | 100 |
| | 1 | 3 | 40 | 4 | 0 | 3 | 20 | 3 | 95 | 3 | 20 | 3 | 40 | — | 100 | 3 | 0 | 3 | 0 | 3 | 60 | 3 | 80 | 3 | 90 |
| | 0.5 | 4 | 0 | 5 | 0 | 5 | 0 | — | 100 | 4 | 0 | 5 | 0 | 3 | 60 | 4 | 0 | 5 | 0 | 5 | 0 | 4 | 0 | 5 | 0 |
| 10 | 4 | — | 100 | 5 | 0 | 3 | 60 | — | 100 | — | 100 | — | 100 | — | 100 | — | 100 | 1 | 95 | — | 100 | 1 | 95 | — | 90 |
| | 2 | — | 100 | 5 | 0 | 4 | 40 | — | 100 | 4 | 50 | 4 | 0 | — | 100 | — | 60 | 3 | 40 | — | 100 | 3 | 60 | 3 | 50 |
| | 1 | 3 | 30 | 5 | 0 | 4 | 0 | — | 95 | 4 | 0 | 5 | 0 | 4 | 70 | 4 | 20 | 4 | 0 | — | 100 | 4 | 0 | 5 | 0 |
| | 0.5 | 5 | 0 | 5 | 0 | 5 | 0 | 3 | 20 | 5 | 0 | 5 | 0 | 5 | 0 | 5 | 0 | 5 | 0 | 5 | 0 | 5 | 0 | 5 | 0 |
| 11 | 4 | — | 100 | 3 | 0 | — | 100 | — | 100 | — | 100 | — | 100 | — | 100 | — | 100 | 2 | 60 | — | 100 | — | 100 | — | 100 |
| | 2 | — | 100 | 5 | 0 | 1 | 80 | — | 100 | 1 | 80 | 1 | 60 | — | 100 | 3 | 20 | 4 | 0 | 3 | 95 | — | 100 | — | 100 |
| | 1 | — | 100 | 5 | 0 | 3 | 40 | — | 100 | 3 | 40 | 3 | 20 | — | 100 | 4 | 0 | 5 | 0 | 4 | 60 | — | 100 | — | 100 |
| | 0.5 | 3 | 95 | 5 | 0 | 4 | 0 | — | 100 | 3 | 0 | 4 | 0 | 3 | 80 | 5 | 0 | 5 | 0 | — | 0 | 3 | 60 | 3 | 90 |

TABLE II

PRE-EMERGENT ACTIVITY

| PRODUCT OF EXAMPLE NO. | LBS. PER ACRE | Sugar Beets Vig | Sugar Beets % Kill | Corn Vig | Corn % Kill | Oats Vig | Oats % Kill | Clover Vig | Clover % Kill | Soybeans Vig | Soybeans % Kill | Cotton Vig | Cotton % Kill | Mustard Vig | Mustard % Kill | Yellow Foxtail Vig | Yellow Foxtail % Kill | Barnyard Grass Vig | Barnyard Grass % Kill | Crab Grass Vig | Crab Grass % Kill | Buck-Wheat Vig | Buck-Wheat % Kill | Morning-Glory Vig | Morning-Glory % Kill |
|---|---|---|---|---|---|---|---|---|---|---|---|---|---|---|---|---|---|---|---|---|---|---|---|---|---|
| 2  | 2    | — | 100 | 3 | 0 | 1 | 90  | — | 100 | — | 100 | — | 100 | — | 100 | 3 | 80  | 4 | 0  | 4 | 0   | — | 100 | — | 100 |
|    | 1    | — | 100 | 5 | 0 | 3 | 80  | — | 100 | 1 | 100 | — | 100 | — | 100 | 3 | 80  | 4 | 0  | 4 | 0   | — | 100 | — | 100 |
|    | 0.5  | — | 100 | 5 | 0 | 4 | 0   | — | 100 | 1 | 60  | — | 100 | — | 100 | 3 | 30  | 5 | 0  | 5 | 0   | 3 | 100 | 3 | 95  |
|    | 0.25 | — | 100 | 5 | 0 | 5 | 0   | — | 100 | 3 | 0   | — | 100 | — | 100 | 5 | 0   | 5 | 40 | 5 | 100 | — | 80  | 3 | 90  |
| 10 | 2    | — | 100 | 3 | 0 | 1 | 80  | — | 100 | 1 | 80  | — | 100 | — | 100 | — | 100 | 1 | 0  | — | 60  | — | 100 | 4 | 90  |
|    | 1    | — | 100 | 5 | 0 | 3 | 20  | — | 100 | 3 | 0   | — | 100 | — | 100 | 3 | 80  | 5 | 0  | 3 | 0   | 3 | 100 | 4 | 0   |
|    | 0.5  | — | 100 | 5 | 0 | 5 | 0   | 3 | 60  | 4 | 0   | — | 100 | — | 80  | 5 | 0   | 5 | 0  | 5 | 0   | — | 80  | 5 | 0   |
|    | 0.25 | — | 100 | 3 | 0 | 5 | 0   | — | 100 | 5 | 0   | — | 100 | 3 | 100 | 5 | 0   | 3 | 10 | 3 | 95  | — | 100 | — | 0   |
| 11 | 2    | — | 100 | 5 | 0 | — | 100 | — | 100 | — | 100 | — | 100 | — | 100 | 3 | 100 | 4 | 0  | 4 | 10  | — | 100 | — | 100 |
|    | 1    | — | 100 | 5 | 0 | 1 | 80  | — | 100 | 1 | 100 | — | 100 | — | 100 | 3 | 30  | 5 | 0  | 5 | 0   | — | 100 | 1 | 80  |
|    | 0.5  | — | 100 | 3 | 0 | 3 | 20  | — | 100 | 3 | 20  | — | 100 | — | 100 | 5 | 0   | 5 | 0  | 5 | 0   | — | 100 | 3 | 95  |
|    | 0.25 | — | 100 | 5 | 0 | 4 | 0   | — | 100 | 3 | 0   | — | 100 | 3 | 95  | 5 | 0   | 5 | 0  | 5 | 0   | — | 100 | 4 | 60  |

TABLE III

PRE-EMERGENT ACTIVITY

| PRODUCT OF EXAMPLE NO. | LBS. PER ACRE | Sugar Beets | | Corn | | Oats | | Clover | | Soybeans | | Cotton | | Mustard | | Yellow Foxtail | | Barnyard Grass | | Crab Grass | | Buck-Wheat | | Morning-Glory | |
|---|---|---|---|---|---|---|---|---|---|---|---|---|---|---|---|---|---|---|---|---|---|---|---|---|---|
| | | Vig | % Kill | Vig | % Kill | Vig | % Kill | Vig | % Kill | Vig | % Kill | Vig | % Kill | Vig | % Kill | Vig | % Kill | Vig | % Kill | Vig | % Kill | Vig | % Kill | Vig | % Kill |
| 3 | 4 | — | 100 | 1 | 20 | — | 100 | — | 100 | — | 100 | — | 100 | — | 100 | — | 100 | — | 100 | — | 100 | — | 100 | — | 100 |
| | 2 | — | 100 | 2 | 0 | — | 100 | — | 100 | — | 100 | — | 100 | — | 100 | — | 100 | 1 | 90 | — | 100 | — | 100 | — | 100 |
| | 1 | — | 100 | 3 | 0 | — | 100 | — | 100 | — | 100 | 3 | 20 | — | 100 | 1 | 90 | 3 | 95 | — | 100 | — | 100 | — | 100 |
| | 0.5 | 3 | 60 | 4 | 0 | 3 | 20 | 3 | 80 | 3 | 20 | 3 | 0 | 3 | 40 | 3 | 0 | 3 | 0 | 3 | 60 | — | 100 | 4 | 0 |
| 5 | 4 | 4 | 80 | 3 | 20 | — | 100 | — | 100 | — | 100 | — | 100 | — | 100 | — | 95 | 1 | 90 | — | 100 | — | 100 | — | 100 |
| | 2 | 4 | 40 | 4 | 0 | 3 | 95 | — | 100 | 3 | 100 | — | 100 | — | 100 | 3 | 100 | 1 | 95 | — | 100 | — | 100 | — | 100 |
| | 1 | 5 | 0 | 5 | 0 | 3 | 60 | 3 | 95 | 3 | 80 | 4 | 20 | — | 100 | — | 20 | 3 | 90 | 3 | 95 | — | 100 | 4 | 0 |
| | 0.5 | 5 | 0 | 5 | 0 | 4 | 0 | 4 | 40 | 5 | 0 | 5 | 0 | 4 | 0 | 5 | 0 | 3 | 0 | 4 | 0 | 4 | 30 | 5 | 0 |
| 7 | 4 | — | 100 | 2 | 0 | — | 100 | — | 100 | — | 100 | — | 100 | — | 100 | — | 100 | — | 100 | — | 100 | — | 100 | — | 100 |
| 20 | 4 | — | 100 | 3 | 0 | — | 80 | — | 100 | — | 100 | — | 100 | — | 100 | 1 | 20 | — | 100 | — | 100 | — | 100 | — | 100 |
| | 2 | — | 100 | 5 | 80 | — | 100 | — | 100 | — | 100 | — | 100 | — | 100 | — | 100 | — | 80 | — | 100 | — | 100 | 4 | 0 |
| | 1 | 3 | 80 | 5 | 0 | 3 | 0 | — | 100 | 3 | 60 | 4 | 40 | 3 | 95 | 3 | 60 | 1 | 80 | — | 100 | — | 60 | 5 | 0 |
| | 0.5 | 4 | 0 | 5 | 0 | 5 | 0 | — | 100 | 5 | 0 | 5 | 0 | 5 | 0 | 4 | 0 | 3 | 20 | 3 | 95 | 5 | 0 | 5 | 0 |

TABLE IV

POST-EMERGENT ACTIVITY

| PRODUCT OF EXAMPLE NO. | LBS. PER ACRE | Sugar Beets | | Corn | | Oats | | Clover | | Soybeans | | Cotton | | Mustard | | Yellow Foxtail | | Barnyard Grass | | Crab Grass | | Buck-Wheat | | Morning-Glory | |
|---|---|---|---|---|---|---|---|---|---|---|---|---|---|---|---|---|---|---|---|---|---|---|---|---|---|
| | | Vig | %Kill | Vig | %Kill | Vig | %Kill | Vig | %Kill | Vig | %Kill | Vig | %Kill | Vig | %Kill | Vig | %Kill | Vig | %Kill | Vig | %Kill | Vig | %Kill | Vig | %Kill |
| 3 | 2 | — | 100 | — | — | — | 100 | — | 100 | — | — | — | 100 | — | — | — | 100 | — | — | — | — | — | 100 | — | — |
|   | 1 | — | 100 | — | — | — | 100 | — | 100 | — | — | — | 100 | — | — | — | 100 | — | — | — | — | — | 100 | — | — |
|   | 0.5 | — | 100 | — | — | 1 | 80 | — | 100 | — | — | — | 100 | — | — | — | 100 | — | — | — | — | — | 100 | — | — |
|   | 0.25 | — | 100 | — | — | 3 | 0 | — | 100 | — | — | — | 100 | — | — | 2 | 80 | — | — | — | — | — | 100 | — | — |
| 5 | 2 | — | 100 | 4 | 0 | — | 100 | — | 100 | — | 100 | — | 100 | — | 100 | — | 100 | 1 | 60 | — | 95 | — | 100 | — | 100 |
|   | 1 | 3 | 80 | 5 | 0 | 1 | 90 | — | 100 | 3 | 60 | — | 100 | — | 100 | — | 100 | 3 | 0 | 3 | 30 | — | 100 | 3 | 80 |
|   | 0.5 | 4 | 30 | 5 | 0 | 3 | 0 | — | 100 | 3 | 40 | — | 100 | — | 100 | 3 | 40 | 4 | 0 | 4 | 0 | — | 100 | 4 | 0 |
|   | 0.25 | 5 | 0 | 5 | 0 | 5 | 0 | 4 | 30 | 5 | 0 | 3 | 20 | 3 | 60 | 5 | 0 | 5 | 0 | 5 | 0 | — | 100 | 5 | 0 |

When utilized for herbicidal purposes, compounds of the invention may be formulated in a variety of ways and concentrations for application to the locus of desired vegetation control. It is recognized that the particular type and concentration of formulation, as well as the mode of application of the active ingredient, may govern its biological activity in a given application.

Compounds of the invention may be prepared as simple solutions of the active ingredient in an appropriate solvent in which it is completely soluble at the desired concentration. Such solvent systems include water, alcohols, acetone, aqueous alcohol and acetone, and other organic solvents. These simple solutions may be further modified by the addition of various surfactants, emulsifying or dispersing agents, colorants, odorants, anti-foaming agents, other herbicides or herbididal oils which supplement or synergize the activity of the herbicides of the invention, or other adjuvants for any given application where deemed desirable to impart a particular type or degree of plant responses.

Compounds of the invention may also be formulated in various types of formulations commonly recognized by those skilled in the art of agricultural or industrial chemicals. These formulations include, for example, compositions containing the active ingredient as granules of relatively large particle size, as powder dusts, as wettable powders, as emulsifiable concentrates or as a constituent part of any other known type of formulation commonly utilized by those skilled in the art. Such formulations include the adjuvants and carriers normally employed for facilitating the dispersion of active ingredient for agricultural and industrial applications of phytotoxicants. These formulatiosn may contain as little as 0.25% or more than 95% by weight of the active ingredient.

Dust formulations are prepared by mixing the active ingredient with finely divided solids which act as dispersants and carriers for the phytotoxicant in applying it to the locus of applications for vegetation control. Typical solids which may be utilized in preparing dust formations of the active ingredients of the invention include talc, kieselguhr, finely divided clay, fullers' earth, or other common organic or inorganic solids. Solids utilized in preparing dust formulations of the active ingredient normally have a particle size of 50 microns or less. The active ingredient of these dust formulations is present commonly from as little as 0.25% to as much as 30% or more by weight of the composition.

Granular formulations of the active ingredients are prepared by impregnating or adsorbing the toxicant on or into relatively coarse particles of inert solids such as sand, attapulgite clay, gypsum, corn cobs or other inorganic or organic solids. The active ingredient of these granular formulations is commonly present form 1.0% to as much as 20.0% or more by weight of the composition.

Wettable powder formulations are solid compositions of matter wherein the active ingredient is absorbed or adsorbed in or on a sorptive carrier such as finely divided clay, talc, gypsum, lime, wood flour, fullers' earth, kieselguhr, or the like. These formulations preferably are made to contain 50% to 80% of active ingredient. These wettable powder formulations commonly contain a small amount of a wetting, dispersing or emulsifying agent to facilitate dispersion in water or other liquid carrier utilized to distribute the phytotoxicant to the locus of desired vegetation control.

Emulsifiable concentrate formulations are homogeneous liquid or paste compositions containing the active ingredient which will disperse in water or other liquid carrier to facilitate application of the phytotoxicant to the locus of desired vegetation control. Such emulsifiable concentrate formulations of the active ingredients may contain only the active ingredient with a liquid or solid emulsifying agent or may contain other relatively nonvolatile organic solvents such as isophorone, dioxane, heavy aromatic naphthas, xylene, or dimethyl formamide. The active ingredient in such formulations commonly comprises 10.0% to 70.0% by weight of the phytotoxicant composition.

In place of the particular composition employed to produce the products of the invention, this composition may also be employed to produce the products having substantially the same degree of biological activity.

What is claimed is:

1. Compounds having the formula:

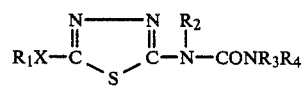

wherein
X is a $SO_2$ radical
$R_1$ is a lower alkyl radical having from 1 to 4 carbon atoms,
$R_2$ is a lower alkyl radical having from 1 to 4 carbon atoms.
$R_3$ is a lower alkyl radical having from 1 to 4 carbon atoms or an alkoxy radical having from 1 to 4 carbon atoms, and
$R_4$ is hydrogen or a lower alkyl radical having from 1 to 4 carbon atoms.

2. The compound of claim 1 wherein X is $SO_2$, $R_1$ is n-$C_4H_9$, $R_2$ is $CH_3$, $R_3$ is $CH_3$ and $R_4$ is H.

3. The compound of claim 1 wherein X is $SO_2$, $R_1$ is $CH_3$, $R_2$ is $CH_3$, $R_3$ is $CH_3$ and $R_4$ is H.

4. A compound as in claim 1 wherein $R_3$ is a lower alkyl radical having from 1 to 4 carbon atoms.

5. A compound as in claim 1 wherein $R_1$, $R_2$ and $R_3$ are each methyl and $R_4$ is n-butyl.

6. A compound as in claim 1 wherein $R_1$ is sec-butyl, $R_2$ and $R_3$ are each methyl and $R_4$ is hydrogen.

7. A compound as in claim 1 wherein $R_1$ is n-propyl, $R_2$ and $R_3$ are each methyl and $R_4$ is hydrogen.

8. A herbicidal composition containing an agriculturally acceptable carrier and at least one compound having the formula:

wherein
X is a $SO_2$ radical,
$R_1$ is a lower alkyl radical having from 1 to 4 carbon atoms,
$R_2$ is a lower alkyl radical having from 1 to 4 carbon atoms,
$R_3$ is a lower alkyl radical having from 1 to 4 carbon atom or an alkoxy radical having from 1 to 4 carbon atoms, and
$R_4$ is hydrogen or a lower alkyl radical having from 1 to 4 carbon atoms.

9. A composition as in claim 8 wherein $R_3$ is a lower alkyl radical having from 1 to 4 carbon atoms.

10. A composition as in claim 8 wherein $R_1$, $R_2$ and $R_3$ are each methyl and $R_4$ is n-butyl.

11. A composition as in claim 8 wherein $R_1$ is sec-butyl, $R_2$ and $R_3$ are each methyl and $R_4$ is hydrogen.

12. A composition as in claim 8 wherein $R_1$ is n-propyl, $R_2$ and $R_3$ are each methyl and $R_4$ is hydrogen.

13. A method for controlling undesirable vegetation which comprises applying to the locus of the vegetation a herbicidally effective amount of a compound of claim 1.

14. A method for controlling undesirable vegetation which comprises applying to the locus of the vegtation a herbicidally effective amount of a composition of claim 8.

15. The composition of claim 8 wherein X is $SO_2$, $R_1$ is $n-C_4H_9$, $R_2$ is $CH_3$, $R_3$ is $CH_3$ and $R_4$ is H.

16. The composition of claim 8 wherein X is $SO_2$, $R_1$ is $CH_3$, $R_2$ is $CH_3$, $R_3$ is $CH_3$ and $R_4$ is H.

* * * * *